United States Patent [19]

Batterbury et al.

[11] Patent Number: 5,739,102
[45] Date of Patent: Apr. 14, 1998

[54] WOUND HEALING

[75] Inventors: Mark Batterbury, Wilmslow; Ian Grierson, Moreton; Paul Stephenson Hiscott, Hoylake, all of England

[73] Assignee: British Technology Group Limited, London, England

[21] Appl. No.: 795,958

[22] Filed: Feb. 4, 1997

[30] Foreign Application Priority Data

Apr. 19, 1996 [GB] United Kingdom ............ 9608145

[51] Int. Cl.$^6$ .................. A01N 34/18; A61K 38/00; A61K 38/16; A61K 6/00
[52] U.S. Cl. ............................ 514/2; 514/8; 514/863; 514/944; 424/401; 424/701
[58] Field of Search ........................ 514/2, 8, 863, 514/944; 424/401, 701

[56] References Cited

U.S. PATENT DOCUMENTS

| | | | |
|---|---|---|---|
| 4,217,341 | 8/1980 | Suddick | 424/48 |
| 4,421,746 | 12/1983 | Kojima | 424/195 |
| 4,440,761 | 4/1984 | Kojima | 424/195 |
| 4,742,046 | 5/1988 | Bliah | 514/8 |

FOREIGN PATENT DOCUMENTS

| | | |
|---|---|---|
| 173092 A | 3/1986 | European Pat. Off. . |
| 295955 A | 12/1988 | European Pat. Off. . |
| 61-205218 A | 9/1986 | Japan . |
| WO 94/06462 A | 3/1994 | WIPO . |

OTHER PUBLICATIONS

H. Asaga and K. Yoshizato, "Recognition of Collagen by fibroblasts through cell surface glycoproteins reactive with *Phaseolus vulgaris* lectin", *J. Cell Sci. 101*, 625–633 (1992).

A. Mazure and I. Grieson, "In vitro studies of the contractility of cell types involved in proliferative vitreoretinopathy", Investigative Ophthalmology and Visual Science 33, 3407–3415 (1992).

Yu et al., "Reversible inhibition of proliferation of epithelial cell lines by *Agaricus biporus* (edible mushroom) lectin", Cancer Res. 53, 4627–4632 (1993).

Batterbury et al., "Investigation of mushroom lectin as a modulator of ocular wound healing", Investigative Ophthalmology and Visual Science 37, No. 3, Abstract No. 5138 (Feb. 23, 1996).

Batterbury et al., "Investigation of mushroom lectin as a modulator of ocular wound healing", ARVO Home Page or World Wide Web (Feb. 5, 1996).

Primary Examiner—Cecilia J. Tsang
Assistant Examiner—Jennifer Harle
Attorney, Agent, or Firm—Nixon & Vanderhye

[57] ABSTRACT

The rate of healing of a wound can be delayed or anomalous wound healing inhibited by applying an *Agaricus bisporus* lectin (agglutinin) to the site of the wound.

5 Claims, 4 Drawing Sheets

WOUND HEALING

BACKGROUND OF THE INVENTION

1. Field of the Invention

This invention relates to modulating wound healing in a patient.

2. Description of the Related Art

The extracellular matrix, lying between cells, contains fibrillar collagens, which are synthesised by fibroblast cells. They are involved in the contraction of tissue which is an inevitable part of wound healing. Contraction helps to close tissue defects, but excessive contraction leads to tissue deformity and distortion. An important in vitro test for the ability of an agent to inhibit scarring and promote optimal wound healing is that when fibroblast cells, cultured with the agent, are seeded into a collagen gel, the contraction of collagen is inhibited.

The collagen gel culture of fibroblasts in the presence of lectins has been described by H. Asaga, J. Cell Sci. 101, 625–633 (1992). Lectins are a group of proteins of non-immunological origin capable of binding specifically to carbohydrate groups present on cell surfaces. They are not a homogeneous class in their other properties. Thus, many lectins are mitogens, i.e. they stimulate the proliferation of cells. Examples are peanut agglutinin (PNA) and conconavalin A (Con-A). On the other hand, *Agaricus bisporus* agglutinin or lectin (ABA or ABL) has been shown to inhibit the proliferation of keratinocytes (which are epidermal cells), see PCT Application WO94/06462 (British Technology Group Ltd.), and L. Yu et al., Cancer Res. 53, 4627–4632, 1993. *Phaseolus vulgaris* (red kidney bean) lectin, also called phytohaemagglutinin (PHA), consists of an erythroagglutinin of low mitogenic activity (PHA-E) and a leucoagglutinin of high mitogenic activity (PHA-L). Con-A inhibits the infectivity of herpes simplex virus type 1, whereas phytohaemagglutinin P (PHA-P), wheat germ agglutinin (WGA) and pokeweed mitogen (PWM) had no such effect, see Ito and Barron, J. Virol. 13, 1312–1318 (1974), as reported in European Patent Application Publication 173 092 A, at page 3.

H. Asaga et al., supra, tested a variety of lectins for their ability to influence the interactions between cell surface receptors and collagen. For this purpose they used a collagen gel culture test. Human skin fibroblasts from explants of the normal dermis were suspended in a solution containing a lectin and mixed with a collagen gel preparation so that the fibroblasts became embedded in the gel. The extent of contraction of collagen gel during culture was measured. The lectins Con-A, WGA, *Ricinus communis* agglutinin-60 (RCA), *Phaseolus vulgaris* agglutinin (PHA), *Pisum sativum* agglutinin (PSA) and lentil seed agglutinin (LCA) inhibited the fibroblast-mediated collagen gel contraction. However, other lectins, namely soybean agglutinin (SBA), *Agaricus bisporus* agglutinin (ABA), peanut agglutinin (PNA) and pokeweed mitogen (PWM) did not affect gel contraction.

SUMMARY OF THE INVENTION

Contrary to the paper by H. Asaga et al., it has now surprisingly been found that *Agaricus bisporus* agglutinin (ABA=ABL) does inhibit the contraction of collagen gel by fibroblasts and is therefore of use in modulating fibroblast-dependent aspects of wound healing. In particular, ABA inhibits wound healing and the contractile process. Since cell-dependent collagen contraction plays an important role in the rate of wound healing the slowing down of the rate of such contraction is important in inhibiting scar formation and delaying wound healing.

In one aspect, therefore, the present invention provides a method of reducing the rate of wound healing or of inhibiting anomalous wound healing in a patient, which comprises applying to the site of the wound in the patient an effective amount of ABL.

One type of wound in relation to which the present invention is particularly useful is that occurring in eye surgery to reduce intraocular pressure in glaucoma cases. Another is to inhibit retinal scarring following a tear in the retina.

DESCRIPTION OF THE PREFERRED EMBODIMENTS

Figure 1:
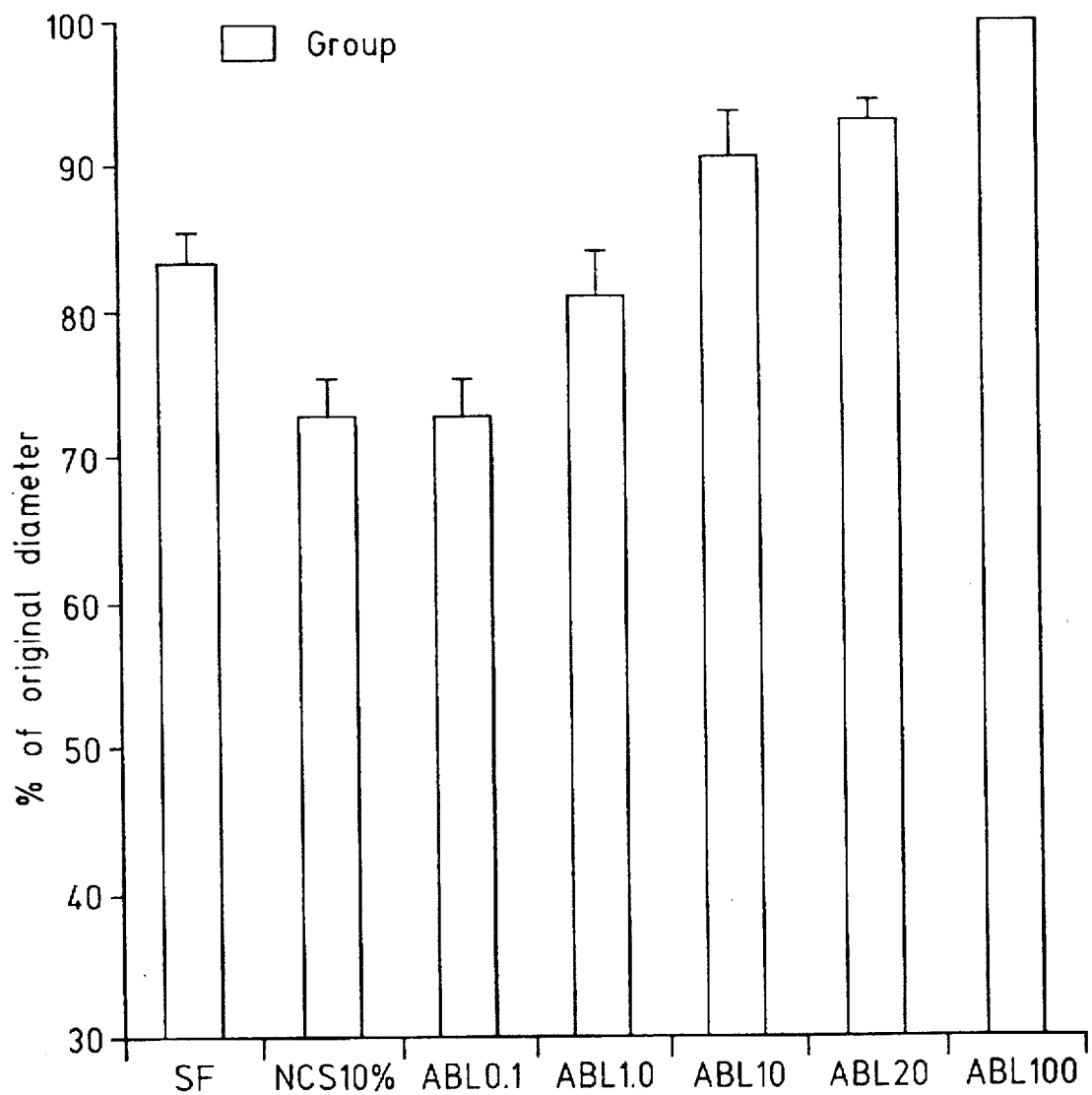
FIG. 1 is a bar chart showing the percentage contraction of collagen gels, seeded with ocular fibroblasts, cultured in the gel in two control media (the two left hand-most) and ascending concentrations of ABL (the five right hand-most).

Although arising from ophthalmology, the invention applies to fibroblast cells in a general sense, including dermal fibroblasts and not just to ocular fibroblasts. It is particularly applicable to wounding by damage to or removal of skin, including through burns and including keloid formation (raised scars on skin).

The particular use in eye surgery for glaucoma cases will now be described. The aim of the surgery is to relieve pressure in the eye, by making an opening to drain away the intraocular fluid (so-called "aqueous humour"). The aqueous humour fills the cavity below the cornea, to the front of the eye, and the lens. The aim is to draw the aqueous humour away slowly by making a valve-like opening in the eye. The hole in the eye is covered by layers of ocular tissue (sclera and conjunctiva), which constitute the flap of a flap valve in this analogy. Unfortunately, in some patients progressive scar tissue formation occurs, which closes off the valve, with consequent re-elevation of pressure in the eye and thus progression of glaucoma.

Current research efforts have been directed towards applying available pharmacological agents, such as the antimetabolites 5-fluorouracil (5-FU) and mitomycin-C, to inhibit scar tissue formation. These drugs are directed at the fibroblast, which has a central role in healing. However such agents are only variably effective, but also are toxic, even to the extent of causing vision impairment themselves.

The drainage site represents an unusual wound, a compromise between complete and inadequate healing. Long term surgical success requires that this compromise, an arrested healing process, be achieved. It is therefore essential that modulators be developed which help reach this objective. Such modulators should be non-toxic, titratable (give a dose-dependent effect) and reversible. ABL fulfils these requirements. Although it is an unusual wound, it is a valuable model for any situation where fibroblast tissue is involved and slow healing is considered beneficial.

In another preferred aspect, the invention relates to the healing of wounds in retinal pigment epithelial (RPE) cells. The RPE cell is in a single layer of cells which form the outer part of the retina (the inner part being the neurosensory retina, made up of rods and cones etc.). The RPE cells have the ability to migrate and transform. A retinal detachment is a detachment of the neurosensory retina from the RPE, usually caused by a tear in the retina. It is corrected by surgery. The most significant complication of retinal detachment surgery is the formation of a scar tissue-like membrane, usually on the surface of the retina, which contracts, preventing the retina from re-attaching or pulling it off again. (This is a form of anomalous wound healing.) The cell which is responsible for the formation of this membrane and for its contraction is the RPE cell.

This kind of scar tissue may also form in the absence of retinal detachment (as a consequence of intraocular inflammation or vascular occlusion, for example) and may form in association with diabetic retinopathy, when it may result in retinal detachment. Thus, there are many occasions when it is important to be able to inhibit growth of this scar tissue-like membrane, particularly if the success of surgery is to be improved.

Currently there is even less scope to modify healing at the retina than there is in the subconjunctival area following glaucoma drainage surgery: 5-FU and mitomycin-C cannot be injected into the vitreous cavity or be applied to the retina. The use of ABL is therefore proposed to inhibit this scar formation.

The ABL may be administered to the site of the wound, in a variety of ways, including (but not limited to) surface or topical application, using e.g. a pad or sponge as applicator. It can be formulated as a suspension or solution for this purpose. Alternatively it can be applied as a cream, ointment or gel formulation. A cream or ointment formulation will normally require an oleaginous vehicle, while a gel will more usually be predominantly aqueous. Any of the bases known for these purposes in pharmaceutical formulations may be used, depending on the site of the wound. Alternatively, the ABL may be injected as a sterile formulation, preferably an aqueous solution, e.g. in physiological saline, or as a suspension. It may be applied as a sustained release mini-capsule or in a shaped polymeric form of size and shape appropriate for insertion or around the wound etc., the polymer providing a matrix for slow release of the ABL. Wound dressings, such as bandages, plasters, etc. may be impregnated or overlaid with ABL.

In surgical procedures, the ABL may be given pre-operatively, per-operatively (during the operation) and/or as soon as possible post-operatively. Wounds are best treated whilst still active, i.e. within 3 months for a normal surgical wound. A particular advantage of the invention is that ABL halts or slows contraction already begun which makes it valuable in post-operative wound healing. A surgical wound from a glaucoma operation can be examined under the clinical examination microscope (the slit lamp) and additional dose(s) of ABL given, preferably by injection, in amounts carefully judged to be suitable to prevent excessive healing, yet allow the external wound to close completely without closure of the "flap valve" created by the surgery, through which drains the aqueous humour from the eye. In this context, it is particularly valuable and important that ABL permits the collagen to contract in a controlled manner dependent on the dose of ABL.

The dose of ABL is normally in the region of 20–60 µg per dose, with repeat doses given as required to delay wound healing. However, the dose may be varied widely outside this range according to size of wound, mode of administration, whether a slow release form is provided and so on.

The following Examples illustrate the invention.

EXAMPLE 1

A collagen gel contraction test was carried out using the method of A. Mazure and I. Grierson, Investigative Ophthalmology & Visual Science 33, 3407–3415 (1992). Thus, human Tenon's capsule ocular fibroblasts were grown to a stage just before confluency in Ham's F10 medium supplemented with 1% glutamine, 1% penicillin/streptomycin, 0.1% Fungizone (Registered Trade Mark), 3% sodium bicarbonate, 0.4–0.6% 1M NaOH with 10% new born calf serum (NCS). Cells were kept in a humidified 5% $CO_2$ incubator at 37° C., fed twice a week and used for experiments between the third and tenth passage.

The cells were removed from their flasks when pre-confluent using 0.1% trypsin and 0.04% EDTA. Then they were mixed with Ham's F10 medium containing 10% NCS, and centrifuged for 10 minutes at 1,000 rpm. After the supernatant was discarded, the cell pellet was resuspended in serum-free medium. Cell numbers were determined with a Coulter counter (Coulter, Luton, UK). The ocular fibroblast cells were used at a concentration of 240,000 cells per collagen matrix.

A collagen solution will polymerize by raising both the pH and the temperature. To make a 400 µl collagen matrix, 0.14 ml of a concentrated medium (35 ml sterile distilled water, 15 ml×10 MEM, 1.5 ml glutamine, 1.5 ml penicillin/streptomycin, 1.5 ml Fungizone and 4 ml of 7.5% sodium bicarbonate) was quickly mixed with 0.24 ml of a solution of collagen (rat-tail type I, Sigma) prepared by dissolving 100 mg of the collagen in 20 ml of 0.1% glacial acetic acid solution in sterile distilled water and stored at 4° C. The concentrated medium was supplemented with NaOH to adjust the pH of the collagen gel-forming mixture to 7.4. Then 0.1 ml serum-free Ham's F10 containing the appropriate amount of cells was added. The mixture was poured into a 24-well plate, one 400 µl volume per well, which was transferred to a humidified 37° C., 5% $CO_2$ incubator, where the matrix set within 1 minute. After 5–10 minutes, the matrix was overlaid with growth medium (positive controls and test media) and floated by scoring around the collagen with a pipette tip. Medium was not changed before 3 days. Serum-containing NCS 10% and serum-free Ham's F10 CSF) were used as positive controls. Test media consisted of serum-free Ham's F10 containing ABL at five different concentrations, namely 0.1, 1.0, 10, 20 and 100 µg/ml (ABL 0.1 . . . ABL 100).

Contraction was assessed daily by measuring the diameter of each lattice against a scaled grid by side illumination. FIG. 1 shows results after 3 days.

As seen in FIG. 1, the higher concentrations of ABL (10 µg/ml, 20 µg/ml, 100 µg/ml) inhibited gel contraction, so that the diameter was 90–100% of original, while the positive controls contracted to 73–83% of original. It is concluded that ABL is a valuable modulator of wound healing having a key requirement of dose-dependency.

EXAMPLE 2

This Example demonstrates the ability of the effects of ABL to be reversed and its application to be titrated, important properties in the modulation of wound healing.

In this Example four experiments were carried out, as in Example 1 but with the following variations:

| | |
|---|---|
| (a) "NCS 1%" POSITIVE CONTROL | The matrix was overlaid with Ham's F10 medium containing 1% NCS. No ABL was added. Medium was changed on day 3. |
| (b) "NCS-ABL 20" THIS INVENTION | As (a) but on day 3 medium was replaced with serum-free Ham's F10 medium containing 20 µg/ml ABL. |
| (c) "ABL 20" THIS INVENTION | The matrix was overlaid with serum-free Ham's F10 medium containing 20 µg/ml ABL. Medium was changed on day 3. |
| (d) "ABL 20-NCS" THIS INVENTION | As (c), the matrix being overlaid with serum-free Ham's F10 medium containing 20 µg/ml ABL. On day 3, the medium was replaced with Ham's F10 medium containing 1% NCS. Additional contraction occurred. |

Figure 2:
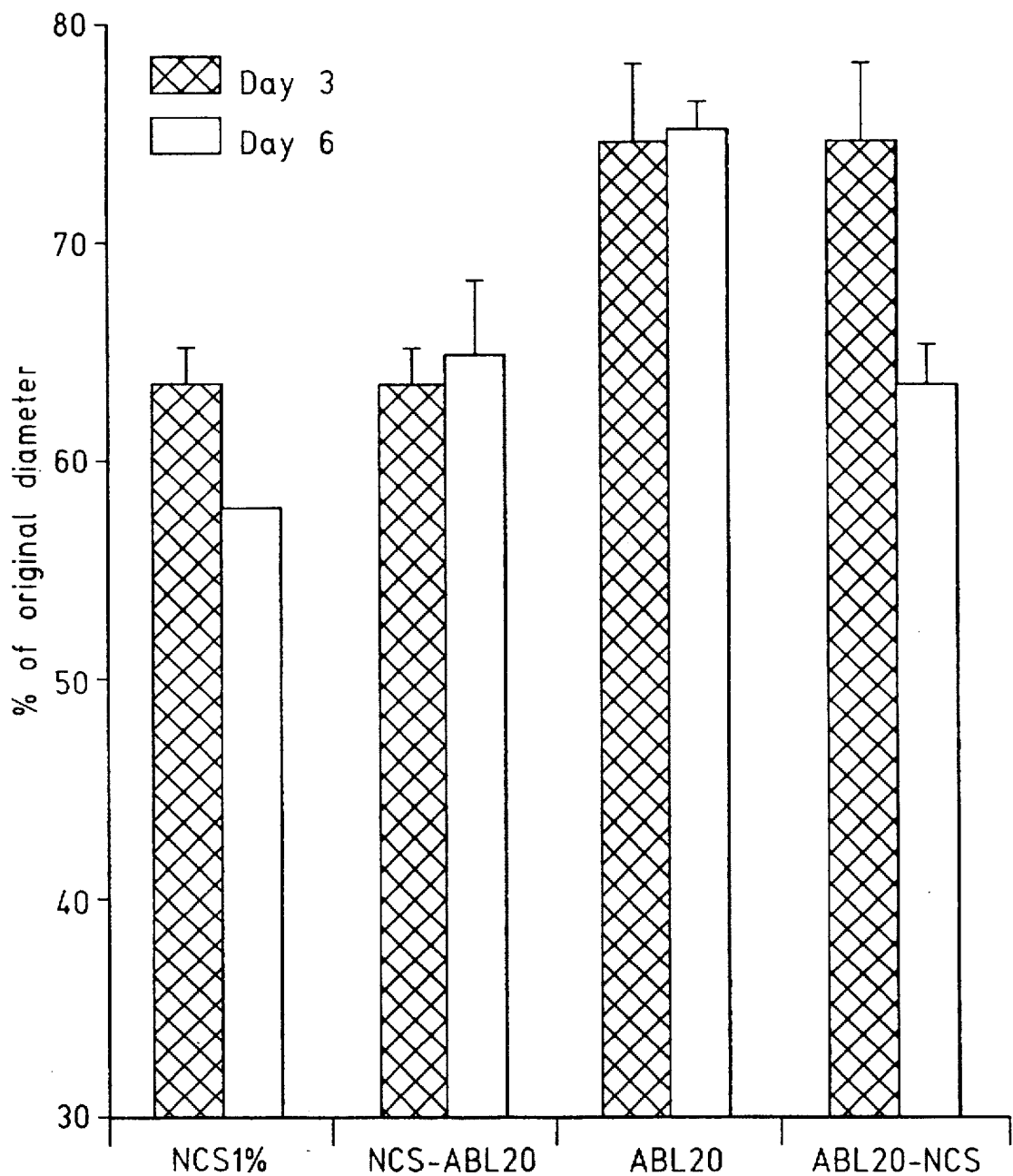
FIG. 2 is a bar chart showing the percentage contraction of collagen gels, seeded with ocular fibroblasts, cultured in the gel under various conditions, for 3 days and also for 6 days, with changes of medium after 3 days.

In FIG. 2, the results are shown in bar chart form as four pairs of bars, the left-hand bar of each pair showing the % contraction after 3 days and the right-hand bar of each pair after 6 days. After 3 days (a) and (b) contracted normally, but (c) and (d) showed inhibition due to ABL. In (a) and (b) the diameter contracted to 63%. In (c) and (d), where ABL was added to the overlaying growth medium, the contraction was dramatically inhibited to only 75% of original.

EXAMPLE 3

Figure 3:
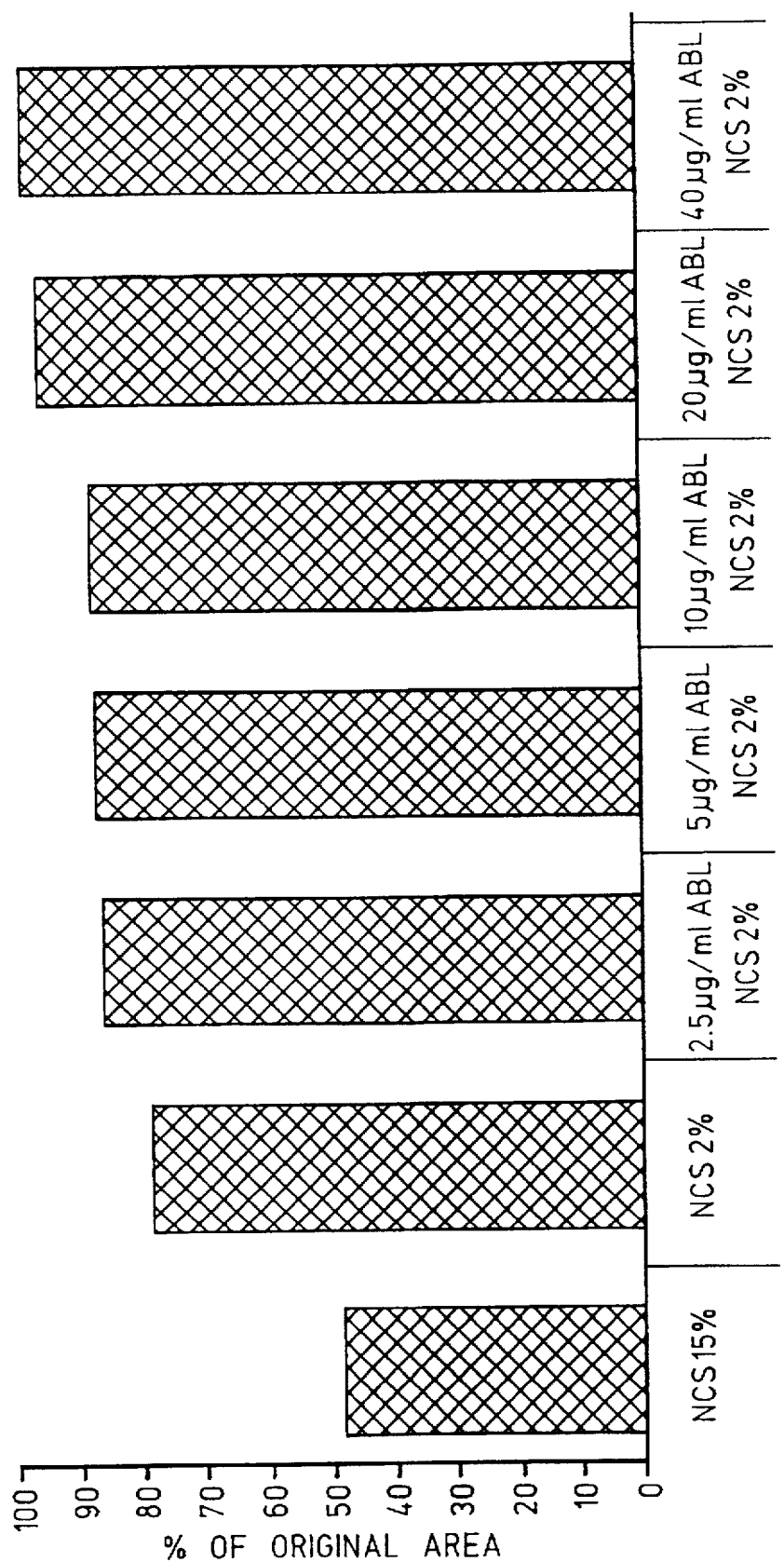
FIG. 3 is a bar chart similar to that of FIG. 1 but relating to retinal pigment epithelial (RPE) cells.

In this Example a different type of cell was used, namely retinal pigment epithelial (RPE) cells. A collagen gel test was carried out similarly to Example 1, except that the matrix was overlaid with MEM (minimum essential medium) containing 2% new born calf serum (NCS) for maintaining the cells in a healthy state. The controls contained 15% and 2% of NCS. In experiments using the present invention the MEM contained 2% NCS plus five different concentrations of ABL, namely 2.5, 5, 10, 20 and 40 µg/ml (ABL 2.5, 5, 10, 20 and 40). As seen in FIG. 3 (bar chart of % original area), the higher concentrations of ABL inhibited gel contraction, so that the diameter was 90–100% of original, while the positive controls shrank to 48% and 78% of original.

EXAMPLE 4

Figure 4:
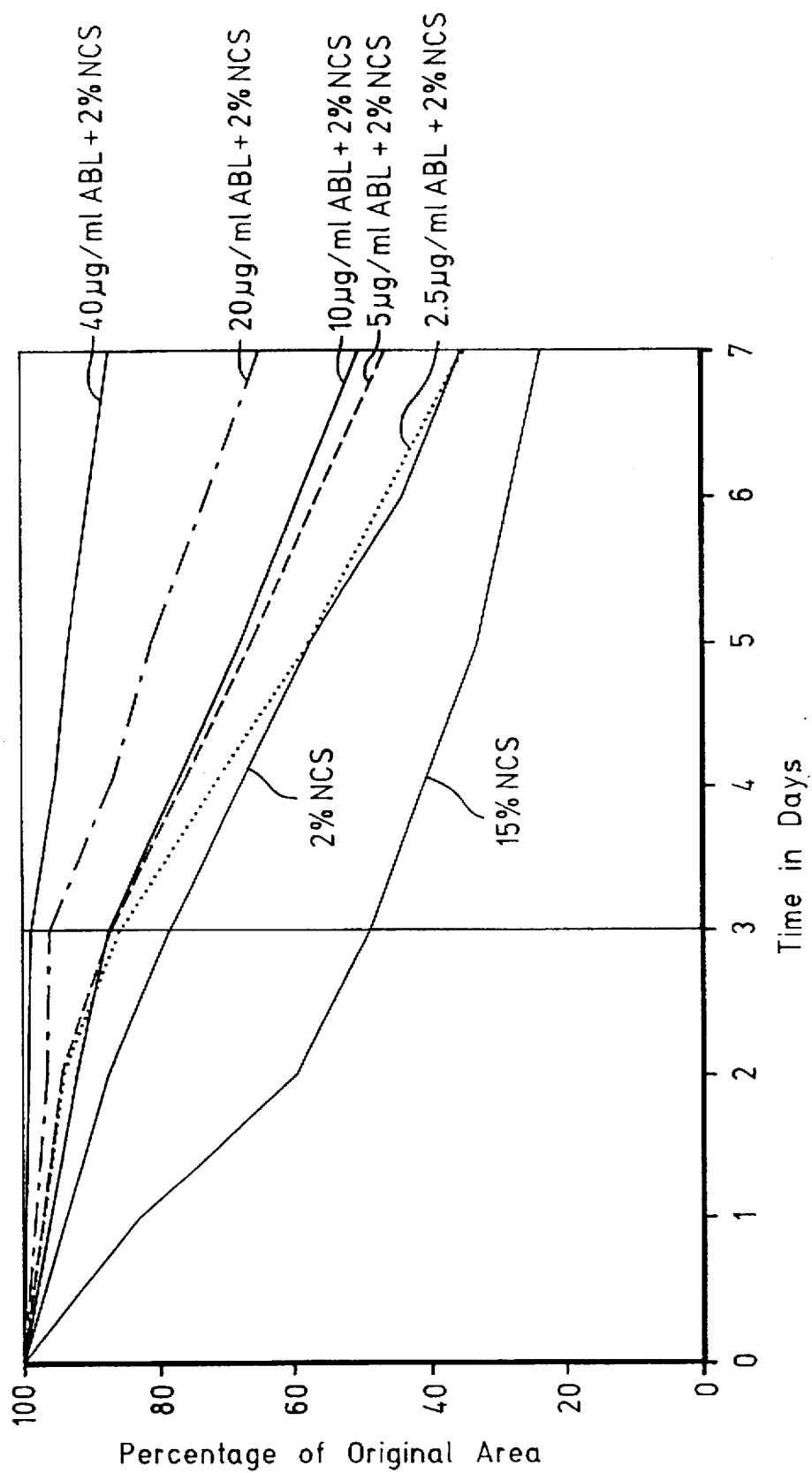
FIG. 4 is a plot of percentage contraction of gels seeded with RPE cells, cultured in the gel under various conditions for 8 days, with a change of medium after 3 days.

The Example shows the ability of the effects of ABL to be reversed and its application to be titrated, with respect to RPE cells. The collagen gel matrix of Example 1 was overlaid with MEM containing:

A. 15% NCS and no ABL
B. 2% NCS and no ABL
C. 2% NCS and 2.5 µg/ml ABL
D. 2% NCS and 5 µg/ml ABL
E. 2% NCS and 10 µg/ml ABL
F. 2% NCS and 20 µg/ml ABL
G. 2% NCS and 40 µg/ml ABL After 3 days, the medium was replaced by MEM containing 15% NCS. As shown in FIG. 4, where % of original area of the gel is plotted on the ordinate and time in days on the abscissa, the higher concentrations of ABL during the first three days reduced the amount of contraction seen in the sample containing no ABL. The addition of the medium containing a higher concentration of NCS reversed this effect and contraction of the gel began to occur.

We claim:

1. A method of reducing the rate of wound healing in a patient in need thereof, which comprises applying to the site of the wound in the patient an effective amount of *Agaricus bisporus* lectin.

2. The method of claim 1 wherein the wound is a surgical operation wound in the eye to relieve pressure in the eye and draw aqueous humour therefrom.

3. The method of claim 1 wherein the lectin is injected into the site of the wound.

4. The method of claim 2 wherein the lectin is applied to the site of the wound per-operatively and/or post-operatively.

5. The method of claim 1 wherein the wound is a wound in the eye resulting from or leading to detachment of the retina from retinal epithelial pigment cells.

* * * * *